United States Patent [19]

Leleu et al.

[11] Patent Number: 5,096,820
[45] Date of Patent: Mar. 17, 1992

[54] PROCESS FOR MANUFACTURING XYLITOL AND XYLITOL-RICH PRODUCTS

[75] Inventors: Jean-Bernard Leleu; Pierrick Duflot, both of Lestrem; Jean-Jacques Caboche, Bethune, all of France

[73] Assignee: Roquette Freres, Lestrem, France

[21] Appl. No.: 592,802

[22] Filed: Oct. 4, 1990

[30] Foreign Application Priority Data

Oct. 4, 1989 [FR] France .................... 89 13003

[51] Int. Cl.$^5$ .................... C12P 7/18; C12P 19/24; C12N 9/04; C07C 51/18
[52] U.S. Cl. .................... 435/158; 435/94; 435/190
[58] Field of Search .................... 435/94, 158, 190

[56] References Cited

U.S. PATENT DOCUMENTS

| | | | |
|---|---|---|---|
| 3,607,652 | 5/1969 | Veda | 435/158 |
| 3,619,369 | 11/1971 | Onishi et al. | 435/158 |
| 3,627,636 | 12/1971 | Jaffe et al. | 435/158 |
| 4,066,711 | 1/1978 | Melaja et al. | 568/872 |
| 4,163,691 | 8/1979 | Devos et al. | 435/174 |
| 4,200,692 | 4/1980 | Puls et al. | 435/99 |
| 4,346,116 | 8/1982 | Verwaerde et al. | 435/95 |
| 4,472,501 | 9/1984 | Takasawa et al. | 435/161 |
| 4,567,142 | 1/1986 | Lloyd | 435/94 |

FOREIGN PATENT DOCUMENTS

| | | | |
|---|---|---|---|
| 2641545 | 7/1990 | France | 435/158 |
| 0013707 | 4/1972 | Japan | 435/158 |
| 0145095 | 7/1985 | Japan | 435/158 |
| 2104588 | 5/1987 | Japan | 435/158 |

OTHER PUBLICATIONS

Chemical Abstracts, vol. 103, No. 17, Oct. 28, 1985, p. 578, Abstract No. 140203p, Columbus, Ohio, U.S.A., S. Ohmomo et al.: "Biotransformation of D-xylulose to Dylose by Immobilized Enzyme Prepared from Streptomyces Flavorirensis", J. Ferment, Technol., 1985, 63(4), 331–5.

Chemical Abstracts, vol. 77, No. 13, Sept. 25, 1972, p. 306, Abstract No. 86674x, Columbus, Ohio, U.S.A., JP-A-72 13707, (H. Onishi), 4/25/72.

Primary Examiner—Herbert J. Lilling
Attorney, Agent, or Firm—Larson and Taylor

[57] ABSTRACT

Process for manufacturing xylitol and xylitol-rich products, characterized in that it consists of:
  enzymatically isomerizing at $M_1$ D-xylulose syrup into syrup containing D-xylose and D-xylulose then, without extracting the xylose,
  catalytically hydrogenating this syrup at $M_2$, resulting thus in a xylitol-rich syrup, said xylitol-rich syrup being either dehydrated, or subjected to chromatographic processing or to a treatment of extraction by crystallization at $M_3$.

8 Claims, 3 Drawing Sheets

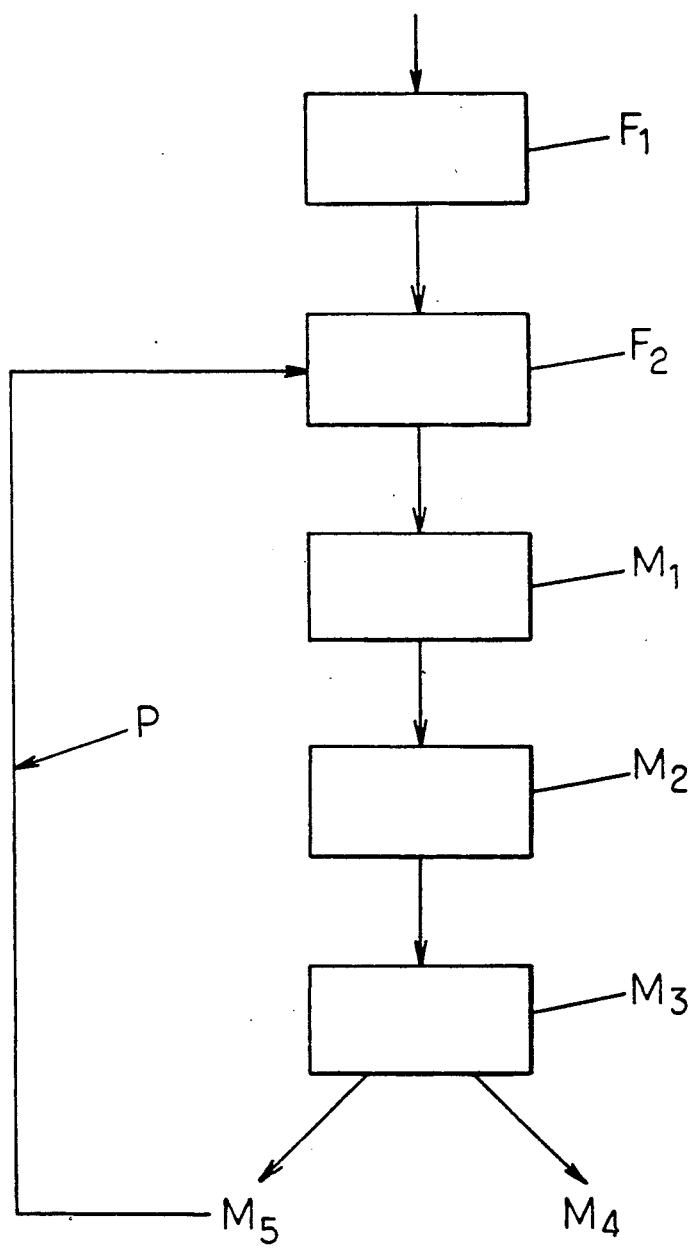

PROCESS FOR MANUFACTURING XYLITOL AND XYLITOL-RICH PRODUCTS

The invention relates to a process for the manufacture of xylitol and xylitol-rich products.

The process of preparing xylitol is known by catalytic hydrogenation of crystalline D-xylose or of syrups rich in D-xylose, this crystalline xylose or these xylose-rich syrups being themselves obtained from plant raw materials such as birch wood, corn cobs, seed husks or almonds.

By acid hydrolysis of these raw materials, under extreme conditions of temperature and pressure, the xylans—D-xylose polymers—are decomposed into xylose whose essential use is, precisely, the manufacture—by hydrogenation—of xylitol.

This process suffers however from numerous drawbacks the principal of which are:

the low xylan content of the raw materials, which is manifested by low yields of xylitol (from 8 to 15% by weight of the raw material employed) and by the generation of a considerable amount of by-products for which it is difficult, even illusory to restore the value and of which the disposal as waste proves to be very polluting, the presence in the hydrolysates of these raw materials of sugars other than xylose, namely those of the group comprising glucose, mannose, galactose and arabinose which are respectively converted by hydrogenation into sorbitol, mannitol, galactitol and arabitol and whose physical properties are close to those of xylitol, which makes it very difficult to separate them from xylitol. Now, the presence of galactitol which occurs normally in the hydrogenated hydrolysates of these plant materials and which crystallizes at the same time as the xylitol when the syrups are concentrated, is undesirable when the xylitol is intended for foodstuff since said galactitol causes cataract.

French patent No. 2,009,331, which describes a process for manufacturing D-arabitol by fermentation of the D-glucose indicates that D-arabitol is an important raw material for preparing D-xylose by passing through D-xylulose; this patent remains however mute on the means which can be employed to convert the D-xylulose into D-xylose and a fortiori into xylitol.

It has also been proposed since 1972, by Japanese patent application No. 47-13707, to prepare xylitol without passing through the intermediate step of D-xylose, by directly hydrogenating D-xylulose formed by aerobic fermentation of D-arabitol, itself obtained by a process according to the above-mentioned French patent No. 2,009,331. The drawback of this process results in the fact that said hydrogenation only provides 50% of xylitol polluted with the same amount of D-arabitol, the latter rendering impossible, when it is present in such proportions, crystallization of the xylitol; this process hence does not permit the preparation of xylitol with high purity and yield. In fact, only D-xylose and its optical isomer, L-xylose, provide 100% of xylitol by catalytic hydrogenation.

An attempt has also been made to obtain, by stereospecific hydrogenation, xylitol with an increased yield from D-xylulose, and it has been discovered recently (J. Ferment. Technol., vol. 66, No. 1, 33–36, 1988) that it was possible to form xylitol with a yield of 75% from D-xylulose. This reduction or stereospecific hydrogenation was only however obtained in 24 hours in a 2% solution of D-xylulose by means of immobilized microorganisms of the Mycobacterium smegmatis genus. It appears clear, in view of the foregoing, that this process is not industrially envisageable due to the fact of the too-considerable duration of the conversion of the D-xylulose into xylitol, of the concentrations used which are too low, of the toxicity problems arising from the mycobacteria employed due to their pathogenic nature for man.

It is also known that enzymatic isomerization of D-xylulose into D-xylose has been performed experimentally by HOCHSTER and WATSON (National Research Council no. 3105 Ottawa, Canada) but the latter have not isolated the D-xylose from the isomerized mixture so obtained and have not proposed either, its use for the manufacture of xylitol. In fact, this isomerization of D-xylulose into D-xylose is still only partial and it had moreover been effected under conditions of temperature and especially of concentration, totally incompatible with industrial use.

In the same way, OHMOMO and his collaborators have proposed the obtaining of a syrup with a very high content of xylose by isomerizing a xylulose syrup obtained from arabitol, but they did not describe the manufacture of xylitol from this syrup. The manufacture of xylose seeming alone to interest them, they also proceded to obtain the maximum richness of xylose on the isomerization of xylulose with very low dry matter of 50 g/l in the presence of large amounts of activator ions and at very high pH, in the vicinity of 9. All these conditions are incompatible with an industrial process since the high dilutions oblige enormous volumes to be treated, because the activator ions are pollutant that should be removed after isomerisation and especially because the pH employed for this isomerisation, if it leads to high contents of xylose, results also in the formation of degradation and epimerisation products which are colored and impossible to remove from the isomerized syrup, making impossible subsequent catalytic hydrogenation that these authors did not, for the rest, envisage.

Consequently, the industrialist still needs a process enabling the production, on the industrial scale, under sanitary conditions and with sufficient purity and yield, of xylitol from D-xylulose, which itself is only obtained with a low yield, close to 40%, from D-glucose by passing through D-arabitol.

It is accordingly a particular object of the invention, to provide a process for the preparation of xylitol from D-xylulose, itself obtained from D-glucose via D-arabitol, suitable for producing xylitol with a sufficiently high yield and purity for the industrialist to be able to undertake the numerous stages leading from D-glucose to the final desired product.

So it is to this problem which has been posed for about 20 years that applicants have had the merit of bringing a solution in discovering that it was possible to obtain xylitol in the state of high purity and under quite advantageous economic conditions by hydrogenating catalytically a D-xylulose syrup previously subjected to an enzymatic isomerisation treatment.

Accordingly, the process of manufacturing xylitol and products rich in xylitol according to invention is characterized in that it consists:

of isomerising enzymatically a D-xylulose syrup into a syrup containing D-xylose and D-xylulose then, without extracting the xylose, of catalytically hydrogenating this syrup, thus resulting in a xylitol-rich syrup, this said syrup rich in xylitol being either dehydrated, or subjected to chromatographic treatment or to an extraction treatment by crystallization.

The D-xylulose can be obtained in manner known in itself and especially by microbiological oxidation of D-arabitol, which constitutes moreover the preferred production process, said D-arabitol being obtained by the aerobic fermentation of D-glucose.

According to an advantageous embodiment, the process of manufacturing xylitol according to the invention is therefore characterized by the fact that the D-xylulose serving as raw material is prepared by a succession of two steps comprising:

aerobic fermentation of D-glucose syrup by means of an osmophilic microorganism of the Pichia genus, converting the D-glucose into D-arabitol, and aerobic fermentation of the D-arabitol by means of a microorganism producing alcohol dehydrogenase, of the genus Acetobacter, Gluconobacter ou Klebsiella, adapted to convert D-arabitol into D-xylulose and thus to provide a D-xylulose-rich syrup.

The aerobic fermentation of D-glucose may be replaced by a modification consisting of passing by oxidation of D-glucose into D-gluconic acid which, in the calcium salt form, can be decarboxylated by the so-called RUFF method to give D-arabinose, as described in U.S. Pat. No. 3,755,294. The D-arabinose is then hydrogenated in manner known in itself to produce D-arabitol.

Despite its apparent complexity, the process according to the invention enables, due to the particular combination of its constituent steps, the production of the xylitol with a yield above 25% and which can reach 40% with respect to the D-glucose which is an abundant raw material of low price.

With respect to the processes of the prior art, the amounts of raw material to be employed and the pollution as well as the volume of by-products generated by the manufacture of the xylitol are considerably diminished.

Other advantages reside in the fact that the logistic problems relating to the collection of the raw material, D-glucose, do not exist, the processing of this raw material can be performed in conventional equipment which does not have to withstand extremely high temperatures and pressures or corrosive environments, the xylitol is obtained free from galactitol and can, consequently, be used in foodstuffs.

Applicants have also discovered that it was possible, and this against all expectation, to improve further the performance of the manufacturing process of the xylitol explained above by subjecting to further fermentation the crystallization mother liquors of the xylitol, rich in xylitol but also in arabitol, by means of the same microorganism producing alcohol dehydrogenase. They have discovered that such a fermented syrup rich in D-xylulose but containing also a high proportion of unconverted xylitol could without problems undergo isomerization under the action of xylose isomerase to provide a syrup rich in D-xylose and in xylitol and this, in spite of the unfavorable teachings which had been given recently by IZUMORI and TUZAKI, "J. Ferment. Technol.", vol. 66, No. 1, 33–36 (1988); these authors had concluded that it appeared indeed that xylitol is a competive inhibitor of xylose isomerase.

On account of the conclusions of IZUMORI and TUZAKI, the presence alone of xylitol in D-xylulose syrups subjected to isomerization, had therefore to make a strong negative influence on the enzymatic isomerization reaction, to be feared.

The isomerized syrup, rich in D-xylose, xylitol and, to a lesser extent, in D-xylulose, can be again hydrogenated to provide a syrup rich in xylitol from which it is convenient to extract the xylitol in its pure and crystalline form.

It is also possible to obtain a xylitol a little less rich by fractionating the hydrogenated syrup by means of a chromatographic process such as described in the French patent No. 2,344,514, for example, this chromatographic fractionation being followed by a treatment of dehydration or of crystallization. The fractionation of said syrup is moreover easy since, contrary to what is explained in this patent with respect to the fractionation of hydrolysates of hydrogenated wood, the process according to the invention provides neither mannitol nor galactitol which would complicate this fractionation. The crystallization mother liquors or the chromatographic fraction rich in D-arabitol are advantageously recycled again to convert the D-arabitol into D-xylulose.

This manner of proceding enables the obtaining, with an unhoped-for yield since it is close to 100%, if one accepts the inevitable losses due to intermediate purifications and concentrations desirable or necessary in the realization of such a process, an almost complete conversion of the D-arabitol into xylitol.

The invention will be still better understood by means of the additional description which follows, of examples and of the accompanying drawing, said additional description, examples and drawing relating to advantageous embodiments of the invention which are not to be taken as limiting.

In the above-said drawing,

FIGS. 2 and 3 illustrate diagramatically two preferred embodiments of the abovesaid process.

Figure 1:
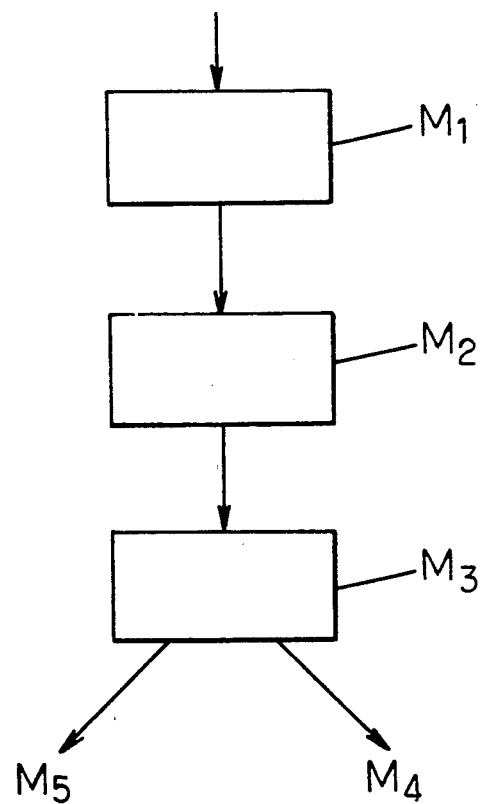
FIG. 1 illustrates diagramatically the process according to the invention.

In FIG. 1, is shown diagramatically:

the enzymatic isomerization of a D-xylulose syrup into syrup rich in D-xylose at $M_1$, the catalytic hydrogenation of this syrup rich in D-xylose to provide a syrup rich in xylitol at $M_2$, the extraction by crystallization of the xylitol from syrup rich in xylitol at $M_3$, this extraction providing xylitol at $M_4$ and mother liquors at $M_5$.

Figure 2:
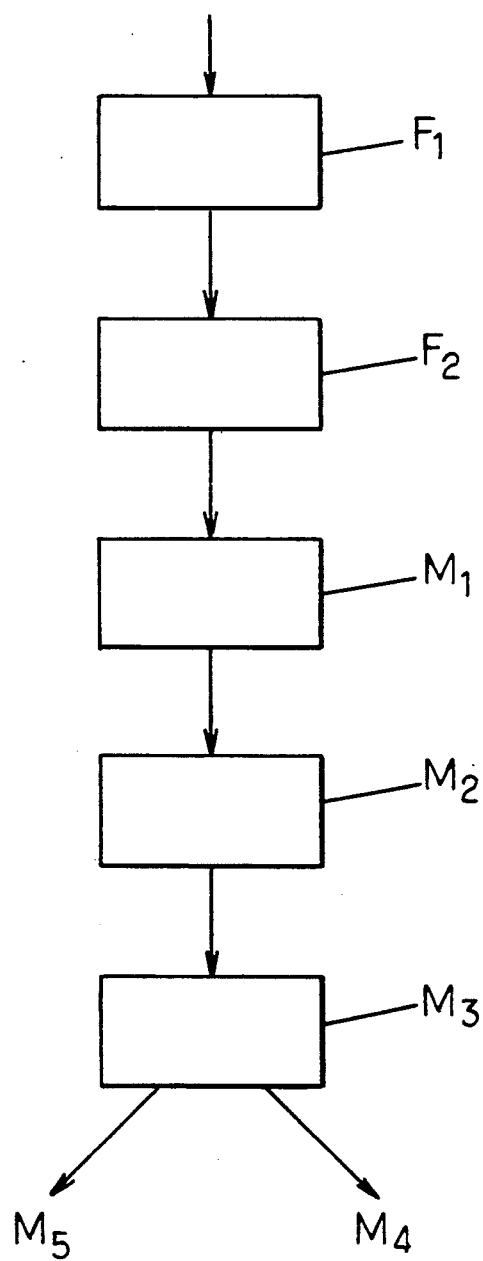

In FIG. 2, is shown diagramatically:

the aerobic fermentation of D-glucose syrup by means of an osmophilic microorganism of the Pichia genus converting the D-glucose into D-arabitol at $F_1$, the aerobic fermentation of D-arabitol by means of a microorganism producing alcohol dehydrogenase of the Acetobacter genus converting the D-arabitol into D-xylulose at $F_2$, at $M_1$, $M_2$, $M_3$, $M_4$, and $M_5$, the steps illustrated by FIG. 1.

In FIG. 3, is shown diagramatically:

the succession of steps $F_1$, $F_2$, $M_1$, $M_2$, $M_3$, $M_4$ and $M_5$ according to FIG. 2, the treatment of the mother liquors from the crystallization ($M_5$) of the xylitol obtained at $M_3$ by a further succession of steps $F_2$, $M_1$, $M_2$, $M_3$, $M_4$ and $M_5$ after recycling at $F_2$ along P.

For the fermentation of the glucose, a culture medium may be resorted to having the following composition:

| dextrose | 150 to 200 g/l |
|---|---|
| organic nitrogen (in the form of corn-steep or yeast extract) | 2 to 4 g/l (N × 6.25) |
| KH₂PO₄ | 1 to 3 g/l |
| MgSO₄, 7H₂O | 1 to 2 g/l | which medium is introduced into a fermenter, then sterilized and inoculated by means of about 10% of a culture for 24 hours of a microorganism of the Pichia genus, for example of the Pichia Ohmeri no. 20.209 strain preserved at the A.T.C.C. (or a strain of *Pichia farinosa*), this culture having been produced in a medium constituted for example as follows:

| dextrose | 50 g/l |
|---|---|
| yeast extract | 10 g/l |
| KH₂PO | 3 g/l |
| MgSO₄, 7H₂O | 1 g/l |

The fermentation is continued at a temperature close to 30° C. for 80 to 100 hours under aeration corresponding to 1 to 1.5 volume of air/volume of culture/minute, and at a pH comprised between 4 and 6, preferably close to 4.5, advantageously maintained by ammonia, due to which there is generally obtained a content of D-arabitol of 65 to 90 g/l, this arabitol representing from 70 to 85% of the matter present in the culture medium at the end of this fermentation, the sugar impurities being particularly constituted by xylitol formed similarly with the arabitol and through non-fermented glucose.

The yield of D-arabitol with respect to the glucose employed is about 45 to 50%.

The entire contents of the fermenter (fermentation must rich in D-arabitol) may then be sterilized so as to destroy the yeast and then be subsequently seeded by an inoculum (about 10%) of an acetobactus suboxydans culture.

It may be advantageous to subject the fermentation must rich in D-arabitol to purification by centrifugation or filtration before seeding with the acetobacter.

In the same way, this purification may be completed by demineralization, a decoloration then concentration enabling crystallization of the D-arabitol with a richness close to 98% and a yield of 40% approximately with respect to the glucose employed.

The D-arabitol obtained in the preceding step may be fermented to a concentration advantageously comprised between 65 and 220 g/l in a culture medium containing organic nitrogen and mineral salts which it is convenient to add all the more importantly as the purification of the arabitol is thorough. The requisite proportions are easily determinable by the technician skilled in the art and will be such that there is obtained about:

| organic nitrogen | 1 to 2 g/l |
|---|---|
| KH₂PO₄ | 1 g/l |
| MgSO₄, 7H₂O | 1 g/l. |

The preculture is advantageously a culture of acetobacter suboxydans cultivated 20 hours approximately on a medium of the following composition:

| arabitol | 50 g/l |
|---|---|
| sorbitol | 2 g/l |
| yeast extract | 2 g/l |
| KH₂PO₄ | 0.2 g/l |
| MgSO₄, 7H₂O | 0.2 g/l |
| CaCO₃ | 5 g/l |

The fermentation of the D-arabitol is conducted at a temperature of 20° to 40° C., under an aeration corresponding to 1 to 1.5 volume of air/volume of culture/minute, at a pH of 4.0 to 6.0 and for a time generally comprised of between 24 and 48 hours, at the end of which period a proportion of 95% of the D-arabitol present in the culture must is converted practically quantitatively into D-xylulose. It is advantageous not to pursue the fermentation beyond this time since there would then be produced degradation products or interconversion products of the sugars or of their derivatives, products of which the accumulation could spoil the subsequent operations.

The mother liquors from the crystallization of the xylitol obtained by the process of the invention may advantageously undergo this fermentation by acetobacter since they are very rich in D-arabitol.

It is observed that the presence of xylitol in large amounts with respect to the arabitol does not interfere with this fermentation as long as the concentration of arabitol+xylitol remains below about 220 g/liter.

In this case, only the D-arabitol is oxidized into D-xylulose by the acetobacter, the xylitol not being oxidized into xylulose but remaining unconverted to the extent that this fermentation is stopped when the D-arabitol represents no more than 1 to 5% of the present sugars.

The glucid composition of the fermentation musts obtained by this action of acetobacter is variable and is a function of the purity of the arabitol, the xylitol present in these musts not being fermentable, nor converted under the conditions described.

This fermentation must can be purified in manner known in itself by filtration, decoloration on activated charcoal and demineralization, and then concentrated before being subject to the isomerization step.

It may be obligatory to resort to the above-said purification if the isomerization is performed continuously by means of an enzyme immobilized in a piston-action reactor; this purification is superfluous in case there follows isomerization batch-wise with lost enzyme and discontinuously.

It is possible to use for the isomerization step a commercial glucose isomerase of the type of those employed for the manufacture of corn syrups with a high content of fructose, namely, for example:

that which is known under the trademark SPEZYME and which is marketed by Suomen Sokeri, that which can be obtained according to French patent No. 2,353,562 whose assignee is the same as the present invention.

Preferably, the amount of enzyme employed is such that the equilibrium of the reaction is reached in 10 minutes to 48 hours according to the continuous or discontinuous technology employed; the presence of a protective agent for the enzyme, such as sodium bisulfide and/or a magnesium salt is desirable.

The isomerization is conducted at a temperature of 40° to 80° C. and at a pH preferably comprised between 6.0 and 8.5.

Generally, the parameters of the isomerization step are selected so that 50 to 75% approximately of the D-xylulose present in the isomerized syrup is converted into D-xylose.

At the end of the isomerization step, the glucid composition of the isomerized syrup obtained varies of course according to the composition of the syrup subjected to isomerization. It is all the richer as the syrup subjected to isomerization was richer in xylitol.

It has been noted with surprise that the presence of xylitol formed in parallel manner to the arabitol during the fermentation of the glucose but essentially caused by the recycling of the mother liquors at the level of the microbiological oxidation step by means of acetobacter in the preferred embodiment of the invention, did not affect the operation of the isomerase glucose since the maximum conversion ratios of the D-xylulose into D-xylose are identical (in the vicinity of 75%) at the levels obtained previously in the isomerization of pure xylose and this fact was completely unexpected, as has already been explained.

The syrup rich in D-xylose obtained after isomerization is purified by demineralization and is then subjected to catalytic hydrogenation by means of ruthenium or Raney nickel catalysts.

Preferably, the hydrogenation step is performed with a Raney nickel catalyst, at a hydrogen pressure above 20 bars and comprised preferably between 40 and 70 bars, at a temperature from 100° to 150° C. and at a concentration of 20 to 60%. The hydrogenation is pursued until the reducing sugar content of the hydrogenated syrup is below 2%, preferably below 1% and more preferably still below 0.5% (the content of reducing sugars being defined by weight of dextrose equivalent with respect to the dry matter).

The hydrogenated syrup so obtained very rich in xylitol, is then filtered to remove the catalyst, then it is demineralized.

The content of xylitol of this hydrogenated syrup, variable according to the composition of the syrup subjected to hydrogenation, is generally above 80% and can exceed 90%.

The syrup can be dehydrated and used as such for technical purposes.

A purer product may be obtained by subjecting said syrup to chromatographic fractionation, for example by using the teachings of the French patent No. 2,344,515; the product thus obtained is subjected to dehydration or crystallization treatment.

To obtain pure xylitol, the above-said syrup is concentrated and then it is cooled again so as to permit the crystallization of the xylitol in one or several crops.

Preferably, the syrup is concentrated to a dry matter content close to 84% and which may be all the lower as the richness in xylitol of the syrup is higher. The concentrated xylitol syrup is then slowly cooled after having been supplemented with crystalline germs of xylitol. It is also possible to add the crystalline germs during the concentration of the xylitol syrup. Preferably, the syrup is cooled to a temperature in the vicinity of 20° C. and with slow stirring.

When the crystallization is completed, which generally occurs at the end of 20 to 90 hours, the crystalline mass so formed is drained and the xylitol crystals are washed then dried.

This xylitol generally has a purity above 97%.

The mother liquors from the crystallization, rich in xylitol but also in arabitol, are generally extracted in one or several crystallization crops to a xylitol content which may be as low as 50, even 45%.

In a preferred embodiment of the process according to the invention, these mother liquors are subjected again to steps of microbial oxidation, enzymatic isomerization, catalytic hydrogenation and crystallization.

Xylitol can also be extracted therefrom by a chromatographic process.

EXAMPLE 1

A D-xylulose syrup obtained from D-glucose via D-arabitol by double fermentation and without crystallization of the latter, was purified by filtration, decoloration and demineralization, and then was concentrated to a dry matter of 25%.

The syrup had the following composition:

| D-arabitol | 1% |
| D-xylulose | 95% |
| D-xylitol | 3% |
| various | 1% |

It was percolated at a temperature of 65° C. over a column of immobilized isomerase glucose of SPEZYME trademark after having been adjusted to a pH of .7.7 by sodium bicarbonate and after the addition of 0.4 g/l of sodium bisulfite and 1 g/l of magnesium chloride.

This syrup was percolated at a flow rate of 3 volumes of syrup/volume of column/hour.

By this isomerization reaction was obtained an isomerized syrup of the following composition:

| D-arabitol | 1% |
| D-xylulose | 25% |
| D-xylose | 70% |
| D-xylitol | 3% |
| various | 1% |

It was observed with surprise that the presence of xylitol formed in a similar manner to arabitol during the fermentation step of the glucose and unconverted at the time of the fermentation of the arabitol into xylulose, did not disturb the operation of the isomerization reaction since the ratio of xylose obtained with respect to the xylulose present in the syrup before isomerization is close to 75%, namely identical with the ratios obtained previously during the isomerization of pure xylose.

This xylose-rich syrup was demineralized then hydrogenated under hydrogen pressure of 50 bars in the presence of Raney nickel and at a temperature of 120° C. After 3 hours of hydrogenation, this syrup showed a content of reducing sugars of 0.1%.

Its composition was then as follows:

| D-arabitol | 13.5% |
| xylitol | 85.5% |
| various | 1% |

This syrup was demineralized then concentrated to a dry matter of 84% and cooled in 30 hours from 60° to 25° C. with slow stirring after having been seeded with crystalline xylitol.

The crystalline mass obtained was drained then washed and pure crystalline xylitol was obtained with a yield of 50% with respect to the dry weight of xylulose syrup employed.

The mother liquors from the crystallization were again concentrated to a dry matter of 86% and were again subjected to crystallization. They provided a second crop of pure crystalline xylitol thus bringing the yield from crystallization to 70%.

The mother liquors from this second crop had the following composition:

| D-arabitol | 45% |
|---|---|
| xylitol | 52% |
| various | 3% |

The crystalline xylitol was thus obtained with a yield of 28% with respect to the glucose employed.

EXAMPLE 2

In a fermenter of total capacity of 10 m³, were introduced:
- 1200 kg of crystalline monohydrate dextrose
- 16 kg of yeast extract
- 8 kg of KH$_2$PO$_4$,
- 8 kg of MgSO$_4$, 7H$_2$O
- 7000 liters of water.

After sterilization of the culture medium and cooling to 30° C., this fermenter was inoculated by means of 800 liters of a preculture of Pichia Ohmeri ATCC 20,209 as described in French patent No. 2,009,331, the preculture being aged for 24 hours.

The aeration was continued throughout the conversion of the glucose into arabitol, namely for 90 hours with a flow rate of 130 Nm³/hour and the pH was maintained by the addition of ammonia, at a value of 4.5.

The fermentation must so obtained was filtered to remove the yeast therefrom, then it was decolorized by activated charcoal and demineralized on exchange resins of the strong cationic resin type followed by a strong anionic resin.

The colorless syrup obtained had the following composition:

| arabitol | 95% |
|---|---|
| xylitol | 3% |
| glucose | 1% |
| various | 1% |

In an evaporator-crystallizer, this purified syrup was concentrated until the production of a thick mass of D-arabitol crystals, then these crystals were drained and washed.

The mother liquors were again concentrated to extract therefrom a second crop of D-arabitol and the latter was obtained in the form of white crystals of 99% richness with a yield of 35% with respect to the glucose employed.

In a fermenter of 10 m³, there were mixed 800 kg of D-arabitol crystals obtained in the preceding step with 800 kg of dry matter from xylitol mother liquors obtained in Example 1, then there were introduced into this fermenter:
- 16 kg of yeast extract
- 8 kg of KH$_2$PO$_4$,
- 8 kg MgSO$_4$, 7H$_2$O
- 6800 liters of water.

The sugar composition of this culture must was as follows:

| arabitol | 72.5% |
|---|---|
| xylitol | 26% |
| various | 1.5% |

After sterilization and cooling, this fermenter was seeded by means of 600 liters of a preculture for 24 hours of acetobacter suboxydans cultivated in a medium of the following composition:

| arabitol | 50 g/l |
|---|---|
| sorbitol | 2 g/l |
| yeast extract | 2 g/l |
| KH$_2$PO$_4$ | 0.2 g/l |
| MgSO$_4$, 7H$_2$O | 0.2 g/l |

After 24 hours fermentation under aeration of 1 volume/volume/minute, the contents of the fermenter were brought to a temperature of 60° C., there were added thereto 3.2 kg of sodium bisulfite and the pH was adjusted to 7.7 by means of sodium carbonate. There were then added thereto 16 liters of liquid glucose isomerase marketed by the Gist-Brocades Company, titrating 4000 international units per ml. After 6 hours of isomerization under these conditions, the composition of the culture medium which was before isomerization:

| xylulose | 71.5% |
|---|---|
| xylitol | 27% |
| various | 1.5% | was established after isomerization at

| xylulose | 18.6% |
|---|---|
| xylose | 52.9% |
| xylitol | 27% |
| various | 1.5% |

It was therefore observed that the presence of very high concentrations of xylitol and of fermentation impurities did not interfere with the isomerization of xylulose into xylose since the conversion ratio was close to 75%.

This syrup was filtered, decolorized and demineralized and then, after having being concentrated to a dry matter of 40% it was hydrogenated under the conditions described in Example 1.

A xylitol syrup of the following composition was obtained:

| xylitol | 89.2% |
|---|---|
| arabitol | 9.3% |
| various | 1.5% |

This syrup can easily be crystallized by the process which was described in Example 1.

EXAMPLE 3

The mother liquors from the second crystallization crop from the xylitol obtained in Example 1 were diluted to a dry matter of 200 g/l and then were supplemented with yeast extract and mineral salts as described in Example 2.

After fermentation with acetobacter suboxydans under the conditions described with regard to Example 2, a culture must was obtained whose sugar composition was as follows:

| xylulose | 43.7% |
|---|---|
| xylitol | 53% |
| various | 3.3% |

Isomerization of this culture must followed as in Example 2 and an isomerized must was obtained whose sugar composition was as follows:

| xylose | 32.4% |
|---|---|
| xylulose | 11.3% |
| xylitol | 53% |
| various | 3.3% |

It was once again observed absolutely surprisingly, that isomerization of D-xylulose into D-xylose was not disturbed by the presence of xylitol which constitutes however the most important component of the must subjected to isomerization.

The isomerized must was filtered and then decolorized and demineralized, when it was concentrated to a dry matter of 40% for hydrogenation which was performed under the conditions described in Example 1.

The hydrogenated syrup so obtained had the following composition:

| xylitol | 91% |
|---|---|
| arabitol | 5.7% |
| various | 3.3% |

Three crystallization crops enabled the extraction in the form of pure and crystalline xylitol of 80% of the material of this syrup subjected to crystallization, thus bringing to 37% the yield of 28% obtained in Example 1 in crystalline xylitol with respect to the glucose employed.

It is evident from the numerical values indicated in these examples that by means of the process according to the invention, crystalline xylitol is obtained from the D-xylulose and hence from D-glucose with a yield that none of the processes using the xylulose route permitted, this yield being moreover much superior to those which could be obtained by hydrolysis processes of vegetable raw material containing xylans.

We claim:

1. Process for manufacturing xylitol and xylitol-rich products, which process consists of:
   enzymatically isomerizing a D-xylulose syrup into a syrup containing D-xylose and D-xylulose and then, without extracting the xylose,
   catalytically hydrogenating this syrup, resulting thus in a syrup rich in xylitol,
said xylitol-rich syrup being either dehydrated, or subjected to chromatographic treatment or to a treatment of extraction by crystallization.

2. Process according to claim 1, wherein the starting D-xylulose syrup is obtained by aerobic fermentation of D-arabitol.

3. Process according to claim 2, wherein the starting D-arabitol is obtained by aerobic fermentation of D-glucose.

4. Process according to claim 2, wherein the D-arabitol is obtained by hydrogenation of D-arabinose.

5. Process for manufacturing xylitol comprising:
   a step of microbiological conversion of D-arabitol into D-xylulose by means of microorganisms producing alcohol dehydrogenase,
   a step of enzymatic conversion of D-xylulose from the preceding step into D-xylose by means of glucose-isomerase,
   a step of catalytic hydrogenation of the D-xylose syrup from the preceding step into a syrup rich in xylitol,
   a step of recovery by crystallization of the xylitol from xylitol-rich syrup from the preceding step and separation of these crystals from their mother-liquors.

6. Process for manufacturing xylitol according to claim 5, wherein the D-arabitol is obtained by microbiological conversion of D-glucose by means of osmophilic yeasts.

7. Process according to claim 5, wherein the mother liquors from which crystalline xylitol has been withdrawn are recycled at the level of the microbiological conversion step of the D-arabitol into D-xylulose.

8. Process according to claim 5, wherein there is used as a raw material mother liquors from which the crystalline xylitol has been extracted.

* * * * *